United States Patent
Jiang et al.

(10) Patent No.: US 7,456,956 B2
(45) Date of Patent: Nov. 25, 2008

(54) VIBRATIONAL CIRCULAR DICHROISM SPECTROMETER USING REFLECTIVE OPTICS

(75) Inventors: Eric Jiang, Fitchburg, WI (US); Francis J. Deck, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 109 days.

(21) Appl. No.: 11/601,344

(22) Filed: Nov. 17, 2006

(65) Prior Publication Data

US 2007/0222988 A1    Sep. 27, 2007

Related U.S. Application Data

(60) Provisional application No. 60/784,741, filed on Mar. 21, 2006.

(51) Int. Cl.
  *G01J 3/28* (2006.01)
  *G01J 3/447* (2006.01)
(52) U.S. Cl. ......................... 356/327; 356/364
(58) Field of Classification Search ............. 356/327
  See application file for complete search history.

(56) References Cited

U.S. PATENT DOCUMENTS 6,480,277 B1   11/2002   Nafie
6,975,397 B2   12/2005   Hug 2003/0175160 A1   9/2003   Archibald et al.

FOREIGN PATENT DOCUMENTS

GB   1 320 662 A   6/1973

OTHER PUBLICATIONS

Nafie, et al., "Vibrational Circular Dichroism of 2,2,2_1_Phenylethanol," J. Am Chem. Soc., p. 3842, (1975).
Nafie, et al., "Vibrational Circular Dichroism," J. Am. Chem. Soc., p. 2715-2723, (1976).
Lipp, et al., "Vibrational Circular Dichroism in the Mid_Infrared Using Fourier Transform Spectroscopy," Chem. Phys. Lett., p. 1-5, (1982).
Wang, et al., "Observations on the Measurement of Vibrational Circular Dichroism with Rapid Scan and Step Scan FTIR Techniques," Applied Spectroscopy, p. 1347-1355, (1995).
Wang, G., "Photoelastic modulator-based vibrational circular dichroism," American Laboratory, p. 36C-36P, (Apr. 1996).
Nafie, L. A., "Vibrational Optical Activity," Appl. Spectrosc., vol. 50 ( No. 5), p. 14A-26A, (1996).

(Continued)

*Primary Examiner*—F. L Evans
(74) *Attorney, Agent, or Firm*—Charles B. Katz; Michael C. Staggs

(57) ABSTRACT

A spectrometer generates Vibrational Circular Dichroism (VCD) measurements having an exceedingly high signal-to-noise ratio, as well as a greater wavelength range over which measurements may be accurately provided. This is achieved by utilizing reflective optics (preferably solely reflective optics, i.e., no refractive elements) to supply a concentrated and collimated input light beam to a sample within a sample cell, and similarly collecting the light output from the sample cell via reflective optics for supply to a detector.

21 Claims, 1 Drawing Sheet

OTHER PUBLICATIONS

Nafie, et al., "Optical Design and Sampling Methods for the Measurement of Vibrational Circular Dichroism using a Nicolet Magna FTIR Spectrometer," Mikrochimica Acta (Suppl.), p. 803-805, (1997).

Dukor, et al., "Vibrational Optical Activity of Pharmaceuticals and Biomolecules," Encyclopedia of Analytical Chemistry, ed. By R.A. Meyers, John Wiley & Sons Ltd, (Chichester, UK), p. 662_676, (2000).

Jiang, E., "Principles, Experiments and Applications: Based on Research_Grade Nicolet FT_IR Spectrometers," Thermo Electron Corporation, (2003).

Wang, "PEM-Based VCD Spectroscopy," Hinds Instruments, (2005).

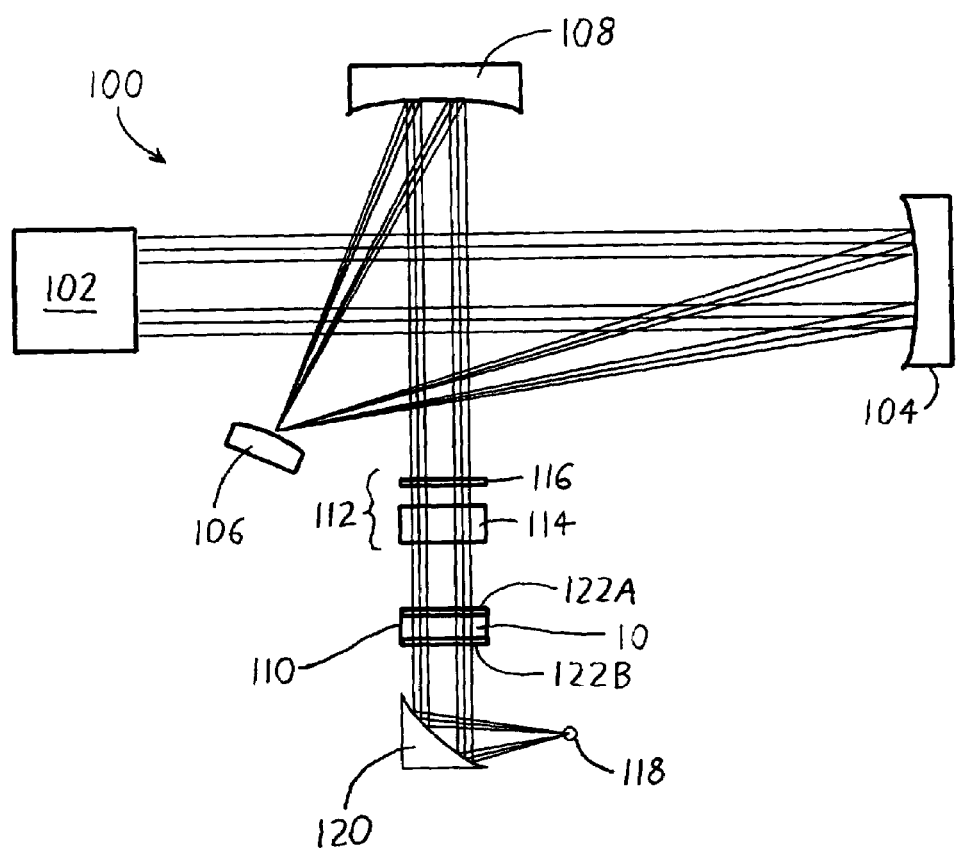

VIBRATIONAL CIRCULAR DICHROISM SPECTROMETER USING REFLECTIVE OPTICS

CROSS-REFERENCE TO RELATED APPLICATIONS

This application claims priority under 35 USC §119(e) to U.S. Provisional Patent Application 60/784,741 filed 21 Mar., 2006, the entirety of which is incorporated by reference herein.

FIELD OF THE INVENTION

This document concerns an invention relating generally to spectrometry, and more specifically to spectrometers for use in measurement of vibrational circular dichroism (VCD), vibrational linear dichroism (VLD), infrared reflection absorption spectroscopy (IRRAS), and other spectrometric measurements wherein the light provided to a sample to be analyzed has modulated polarization.

BACKGROUND OF THE INVENTION

As is well known, spectrometry is a technique wherein light is directed onto a substance to be analyzed, and the resulting light transmitted, reflected, and/or emitted by the sample is then analyzed to provide information about the substance. Vibrational circular dichroism (VCD), or VCD spectroscopy, is a spectrometric technique which uses circularly polarized light to provide information about a substance. As is well known, light is formed from an oscillating electric field—an electric "wave"—and when the field/wave oscillates in a particular way, it is said to be polarized. For example, light having a field oscillating in a plane is said to be plane polarized. Circularly polarized light is then formed when the field oscillates in two perpendicular planes, with the waves in each plane being out of phase, such that the peak of the waves appears to spiral along their direction of travel. When the spiral is oriented counterclockwise when traveling toward a viewer, the light is said to be right-circularly polarized; conversely, if spiraling clockwise, the light is said to be left-circularly polarized.

An interesting feature of many substances is that they respond differently to incident light having different polarization—they may absorb, reflect, and/or transmit different amounts of differently-polarized light. VCD techniques are generally directed to determining the difference in absorption that a substance exhibits between right and left circularly polarized light. VCD measurements are particularly useful in the field of stereochemistry, i.e., the study of the shapes of molecules and the spatial arrangement of atoms therein. More particularly, VCD measurements are useful in the study of substances which contain chiral molecules—molecules having structures which cannot be superimposed on their mirror images. (The concept of chirality is illustrated by a person's right hand, which can be said to be chiral: it is a mirror image of their left hand, but the hands cannot be superimposed no matter how one orients them relative to each other.) As an example, many substances, particularly biological substances, contain chiral molecules of opposite senses—that is, the molecules are mirror images of each other (in which case they are known as enantiomers or optical isomers). Each of the enantiomers may have different properties, in particular, different biological response—for example, sugars are chiral molecules, and the human body can digest and use "right-handed" sugars, but not their left-handed counterparts. Since VCD spectral bands of enantiomers have opposite sign, VCD spectroscopy can allow one to differentiate between enantiomers, a result which is extremely useful in pharmaceutical and chemical fields, among others. Similarly, one can determine how much of one enantiomer is present with respect to its twin, by looking at the spectrum of the mixture of enantiomers and comparing it to one of the "pure" enantiomers (since the difference will reflect how much the spectrum of one enantiomer attenuates the other). Further details on VCD spectrometers, VCD spectrometric techniques, and the uses thereof can be found, for example, in U.S. Pat. No. 6,480,277 to Nafie and in B. Wang, American Laboratory, 36C-36P (April, 1996).

However, VCD spectrometry has numerous drawbacks, some of the most significant being the very small magnitude of the VCD signal from a sample to be analyzed (on the order of $10^{-4}$–$10^{-5}$ absorbance units), and the tendency for measurements to be prone to noise and artifacts (which arise in part owing to the 16w signal magnitude). An associated problem is the time needed to generate a high-quality VCD spectrum: owing to the low signal-to-noise ratio (SNR) in conventional VCD arrangements, VCD measurements must usually be generated in multiple scans (i.e., repeated measurements must be taken), with the measurements then being averaged or otherwise processed to achieve better SNR. These scans can take significant time to execute, with scans sometimes requiring several hours, which is inconvenient. Further, as a result of the need for numerous scans (and significant scan times), VCD measurements of "transient" samples—samples which change over time, e.g., reacting mixtures—are usually not feasible.

SUMMARY OF THE INVENTION

The invention, which is defined by the claims set forth at the end of this document, is directed to methods and devices which at least partially alleviate the aforementioned problems. A basic understanding of some of the preferred features of the invention can be attained from a review of the following brief summary of the invention, with more details being provided elsewhere in this document.

To enhance the reader's understanding, the accompanying FIGURE of the drawings illustrates an exemplary version of the invention. A spectrometer 100 includes a light source 102 (e.g., a lamp with an interferometer or monochromator), and a series of one or more mirrors 104, 106, and 108 which receive the light from the light source 102, and in turn generate a corresponding narrower (and more concentrated) light beam which is input to a sample 10 within a sample cell 110. These drawing depicts an arrangement wherein a concave focusing mirror 104 receives the light from the light source 102 and focuses it onto a convex field mirror 106, and the field mirror 106 then supplies the light to a collimator 108. The collimator 108, which is preferably a mirror rather than a refractive element, at least substantially collimates the light to generate the narrowed input light beam.

A modulator 112 then receives the narrowed input light beam and converts it into a polarization-modulated light beam, i.e., the light is varied between left and right polarization states over time. Preferably, the modulator 112 takes the form of a photoelastic modulator 114 in series with a linear polarizer 116. The modulated light beam is then received by the sample cell 110, which contains the sample 10 to be spectrometrically analyzed. The resulting output light beam is then directed to a photosensitive detector 118, preferably via a focusing mirror 120, with the detector 118 measuring the intensity of the output light beam. The intensity measurements from the detector 118 can then be demodulated at the polarization modulation rate (i.e., the rate at which the modulator 112 alternates the polarization of the input light beam) to obtain the VCD spectrum: the difference between the intensities of the left- and right-circularly polarized light as a function of the wavelength(s) of the input light beam.

As implied by the foregoing discussion, the VCD spectrum is preferably obtained with use of no or few refractive elements (e.g., lenses and prisms), with the arrangement shown in the FIGURE using only mirrors (reflective elements) between the light source 102 and the modulator 112, and between the sample cell 110 and the detector 118. (The polarizer 116 and photoelastic modulator 114, as well as the sample cell 110—particularly its windows B may inherently provide refractive effects.) This is contrary to conventional VCD spectrometry arrangements, wherein the use of lenses (typically zinc selenide or barium fluoride lenses) is preferred because artifacts are believed to arise from the use of reflective elements. Despite the use of reflective elements in the spectrometer 100, it has nonetheless been found to provide very high-quality (high signal-to-noise) VCD measurements more quickly than in conventional arrangements, presumably because (1) the use of reflective elements rather than refractive elements increases light throughput to the sample 10, as well as to the detector 118, and allows higher light capture therefrom, with corresponding higher strength in output signals; and (2) collimation of the light input to the modulator 112 is believed to reduce effects such as surface reflection, vignetting, and polarization retardation (elliptical polarization), and thus measurement artifacts are reduced. Additionally, the spectrometer 100 has greater spectral range than conventional arrangements, most likely because refractive elements can attenuate or cut off light in certain wavelength ranges, whereas reflective elements reduce or eliminate such attenuation. Further, owing to the greater strength (higher signal-to-noise) of the signal measured at the detector 118, fewer scans (wavelength or retardation sweeps of the input light) are needed to compile a strong, well-defined VCD spectrum, which can reduce data collection time by as much as two orders of magnitude. As a result, accurate VCD measurement in kinetic or transient conditions—that is, VCD measurement on samples whose properties may rapidly change along the path of the input beam B can in some cases be possible.

Further advantages, features, and objects of the invention will be apparent from the remainder of this document in conjunction with the associated drawings.

BRIEF DESCRIPTION OF THE DRAWINGS

THE FIGURE is a schematic depiction of a VCD spectrometer 100 utilizing solely reflective optics (a focusing mirror 104, a field mirror 106, and a collimating mirror 108) to supply an input light beam from a light source 102 to a modulator 112 (a linear polarizer 116 and a photoelastic modulator 114) and a sample cell 110, and solely reflective optics (a focusing mirror 120) to supply the output light beam from the sample cell 110 to a detector 118.

DETAILED DESCRIPTION OF PREFERRED VERSIONS OF THE INVENTION

To expand on the foregoing discussion, following is a list of exemplary specific components that can be used in the foregoing arrangement. The light source 102 may be an interferometer and associated components (namely a mid-IR beamsplitter and "Passport" mirror option) taken from a Nicolet 8700 Fourier Transform Infrared (FTIR) spectrometer (Thermo Electron Corp., Waltham, Mass.). The mirrors 104, 106, and 108 can take the form of the following:

focusing mirror 104: concave spherical mirror, 500 mm radius of curvature, 50 mm diameter, preferably gold-coated.

field mirror 106: concave spherical mirror, 180 mm radius of curvature, 25 mm diameter, preferably gold-coated.

collimator 108: concave spherical mirror, 250 mm radius of curvature, 40 mm diameter, preferably gold-coated.

These can be readily custom-made by most lens manufacturers. The modulator 112 may include a Type 5-8321 wire grid IR linear polarizer 116 (Optometrics Corp, Ayer, Mass.), and a Type II/ZS50 photoelastic modulator 114 (Hinds Instruments, Hillsboro, Oreg.). The sample cell 110 may be a conventional sample chamber having dual opposing transmission windows 122A and 122B between which the sample may rest, such as a Type 0018-012 mid-IR liquid sample cell with Type 7000-319 barium fluoride windows (Thermo Electron Corp., Waltham, Mass.). Similarly, the detector 118 may be a conventional photosensitive sensor providing intensity readings across the wavelength range of interest, with a preferred detector being a Type 840-070200 Mercury Cadmium Telluride (MCT) type "A" detector (in a dewar vessel with liquid nitrogen cooling). The focusing mirror 120 may be an off-axis parabolic mirror with 30 mm effective focal length, 90 degree off-axis angle, and 25 mm clear aperture, preferably gold-coated. Such a mirror can be readily custom-made by numerous diamond-turning vendors (e.g., Corning NetOptix, Keene, N.H.). It should be understood that these are merely exemplary components, and others are possible. Control and data collection (including control of the light source 102 and photoelastic modulator 114, capture of the signals from the detector 118, and demodulation of the captured signals at the oscillation rate of the photoelastic modulator 114) can be provided by an appropriately configured and programmed controller, e.g., a personal computer or microcomputer, application-specific integrated circuit (ASIC), or other device (not shown).

The spectrometer 100 can be operated in the following manner. Initially, it is useful to tune/calibrate the spectrometer 100 at initial start-up, and periodically thereafter, for better performance. Tuning may be accomplished by removing the sample cell 110 (or at least removing any sample 10 therefrom), activating the light source 102, and moving the detector 118 in the plane perpendicular to the incoming beam (from the sample cell 110 and focusing mirror 120) to optimize the Channel A signal. (The Channel A signal is the total "raw"/unmodulated signal from the detector 118, in contrast to the Channel B signal, which is the Channel A signal demodulated at the frequency at which the modulator 112—and more specifically its photoelastic modulator 114 B is actuated.) The focusing mirror 120—which is preferably adjustably mounted on a carriage, and fixed in a desired position by use of set screws—can then similarly be moved until a maximum Channel A signal is obtained. A VCD reference sample can then be placed within (or in place of) the sample cell 110; as an example, a quarter-wave plate and linear polarizer may be situated in place of the sample cell 110. This reference sample allows creation of a spectrum (intensity vs. wavelength curve) against which later VCD signals can be normalized. The position of the focusing mirror 120 can then be finely adjusted to maximize the Channel B signal while maintaining the Channel A signal at approximately the same level.

The spectrometer 100 is then ready for use. A desired sample may be situated in the sample cell 110 between its transmission windows 122A and 122B, and Channel A and B interferograms of the sample may then be collected. The "raw" sample VCD spectrum may then be calculated as the ratio $B_s/(A_s*G_s)$ (with proper phase corrections applied), where $B_s$ is the Channel B signal, $A_s$ is the Channel A signal, and $G_s$ is the Gain setting from the demodulator used to generate the Channel B signal. This VCD spectrum can then be reviewed to provide information regarding the properties of the sample.

However, the foregoing "raw" sample spectrum may contain artifacts, which can in turn result in misleading interpretations of the sample properties. As is well known in the field of VCD spectrometry, artifacts are common and can be difficult to compensate for, particularly since it is often uncertain where and how they originate. Following is a preferred method for artifact compensation which has been found to provide useful results.

First, the sample cell 110 is replaced with a reference window having the same thickness as the two sample cell transmission windows 122A/122B together (i.e., if the sample cell transmission windows 122A/122B each have a thickness of L, the reference window preferably has a thickness of 2L). Additionally, the reference window is preferably formed to have the same optical properties as the sample cell transmission windows 122A/122B. Channel A and B interferograms of the reference window may then be collected, and its VCD spectrum may be calculated as the ratio $B_r/(A_r*G_r)$, where $B_r$ is the Channel B signal, $A_r$ is the Channel A signal, and $G_r$ is the Gain setting from the demodulator. The objective of using a single reference window of 2 L thickness in place of the sample cell 110 is to essentially simulate the optical presence of an empty sample cell 110, and thus the resulting VCD spectrum is the "background" spectrum of the spectrometer 100. While it is also possible to simply empty the sample cell 110 rather than substituting a single reference window, an empty sample cell 110 may generate interference from reflections between its transmission windows 122A/122B and thereby generate further artifacts. The sample cell 110 could instead be removed entirely to generate a VCD background spectrum, but in this case the captured spectrum will lack the VCD effects generated by the windows. Nevertheless, in most cases removal of the sample cell 110 will still generate an acceptable background spectrum.

Alternatively, where the raw VCD spectrum is generated from a sample in solution and/or a diluted sample B e.g., from a sample of interest which is dissolved in a solvent B the sample chamber may be filled with the solvent to generate the background spectrum, rather than using the reference window. In this manner, the VCD signal resulting from the solvent is treated as part of the background noise/artifacts. This approach can be extended to solid and gaseous samples as well. For example, some solid samples strongly absorb infrared, which can undesirably result in a saturated signal at the detector 118. This effect can be manageably reduced by thoroughly powdering and mixing the sample with a reference material (such as potassium bromide) before obtaining the raw VCD spectrum. Afterward, the sample chamber may be filled with the reference material to generate the background spectrum, which again treats the VCD signal of the reference material as part of the background noise/artifacts.

Once the raw sample VCD spectrum and background VCD spectrum have been obtained, the background VCD spectrum can be subtracted from the sample VCD spectrum to provide a "cleaned" sample VCD spectrum, one which has reduced noise and artifact content. This cleaned sample VCD spectrum can then be further processed using standard procedures, e.g., normalization, conversion to absorbance units, etc.

A preferred version of the invention has been described above to illustrate a possible way in which the invention might be constructed and operated. However, the invention may take forms other than that of the preferred version described above, and thus a variety of modifications to the foregoing preferred version are possible. Following is an exemplary list of such modifications.

As previously noted, the light source 102 can be a lamp (e.g., tungsten filament lamps, arc lamps, carbon rod lamps, or other light emitters) which supplies an interferometer. In this case, the detected light from the sample—which will contain a range of wavelengths—can be processed using Fourier transform techniques to obtain a spectrum of intensity readings at various wavelengths. Alternatively, a monochromator can be used in lieu of an interferometer, in which case the sample=s response to the monochromatic light can be detected, with the monochromator being scanned through the wavelengths of interest to construct the desired spectrum. Other light source arrangements are also possible.

Modifications to the optical arrangement of the invention are also possible.

Initially, further reflective elements may be utilized, such as folding mirrors (mirrors used to alter the path of the light beam to allow different component layouts, in particular more compact layouts). Some of the reflective elements may be replaced with refractive elements (e.g., the focusing mirror 120 could be replaced with a focusing lens), though use of reflective elements is preferred for the reasons discussed previously. Further, the collimator may be replaced with a focusing mirror (or lens) to focus the input beam onto the sample to adapt the device for applications such as PM-IRRAS (Polarization Modulation Infrared Reflection Absorption Spectroscopy), PM-VLD (Polarization Modulation Vibrational Linear Dichroism), or other spectroscopic methods.

The invention is not intended to be limited to the preferred version of the spectrometer described above, but rather is intended to be limited only by the claims set out below. Thus, the invention encompasses all different versions that fall literally or equivalently within the scope of these claims.

What is claimed is:

1. A spectrometer comprising:
    a) a light source;
    b) one or more mirrors receiving the light from the light source, and generating a narrower light beam therefrom;
    c) a photoelastic modulator receiving the narrower light beam, and generating a polarization-modulated light beam therefrom;
    d) a sample cell receiving the modulated light beam, and generating an output light beam therefrom;
    e) a detector receiving the output light beam.
2. The spectrometer of claim 1 wherein the mirrors include a collimating mirror, whereby the narrower light beam is at least substantially collimated.
3. The spectrometer of claim 2 wherein the mirrors further include:
    a) a concave focusing mirror, and
    b) a convex field mirror, interposed between the collimating mirror and the light source.
4. The spectrometer of claim 2 further comprising an off-axis parabolic mirror interposed between the sample cell and the detector.
5. The spectrometer of claim 1 wherein the mirrors include:
    a) a concave focusing mirror receiving the light from the light source, and
    b) a convex field mirror receiving the light from the focusing mirror.

6. The spectrometer of claim 5 wherein the mirrors further include a collimating mirror receiving the light from the field mirror, whereby the collimating mirror at least substantially collimates the light from the field mirror.

7. The spectrometer of claim 5 further comprising a concave focusing mirror interposed between the sample cell and the detector.

8. The spectrometer of claim 1 wherein no refracting elements are interposed between the light source and the photoelastic modulator.

9. The spectrometer of claim 1 wherein no refracting elements are interposed between the sample cell and the detector.

10. The spectrometer of claim 2 further comprising a linear polarizer interposed between the collimating mirror and the photoelastic modulator.

11. A spectrometer comprising:
   a) a light source;
   b) one or more mirrors receiving light from the light source;
   c) a collimator receiving light from the one or more mirrors;
   d) a modulator receiving light from the collimator, the modulator modulating the light between left and right polarization states;
   e) a sample cell receiving light from the modulator; and
   f) a detector receiving the output light beam.

12. The spectrometer of claim 11 wherein the collimator is a mirror.

13. The spectrometer of claim 12 wherein the one or more mirrors receiving light from the light source include, in series:
   a) a concave mirror receiving light from the light source; and
   b) a convex mirror receiving the light from the concave mirror.

14. The spectrometer of claim 11 wherein the one or more mirrors receiving light from the light source include a concave mirror and a convex mirror.

15. The spectrometer of claim 14 wherein the convex mirror is interposed between the concave mirror and the collimator.

16. The spectrometer of claim 11 wherein the light does not pass through any refractive elements between:
   a) the first of the one or more mirrors, and
   b) the modulator.

17. The spectrometer of claim 11 wherein the light does not pass through any refractive elements between:
   a) the sample cell, and
   b) the detector.

18. The spectrometer of claim 11 further comprising a mirror focusing light from the sample cell onto the detector.

19. The spectrometer of claim 11 wherein the modulator includes:
   a) a linear polarizer, and
   b) a photoelastic modulator.

20. A spectrometric method comprising the steps of:
   a) providing light from a light source to one or more mirrors, the mirrors generating a narrower light beam therefrom;
   b) modulating the polarization of the narrower light beam;
   c) receiving the polarization-modulated light on a sample cell, the sample cell having an output light beam resulting therefrom; and
   d) detecting the intensity of the output light beam.

21. The spectrometric method of claim 20 further comprising:
   a) performing the steps of claim 20 with a sample present in the sample cell;
   b) performing the steps of claim 20 either:
      (1) without the sample present in the sample cell, or
      (2) without the sample cell present,
   c) subtracting the intensity obtained from one of the foregoing steps a, and b from the intensity obtained from the other of the foregoing steps a and b.

* * * * *